US012752043B2

(12) United States Patent
Corazzari

(10) Patent No.: US 12,752,043 B2
(45) Date of Patent: Oct. 6, 2026

(54) SUPPORT MEMBER FOR AN INTEGRATED BLOOD TREATMENT FLUID MODULE

(71) Applicant: B. Braun Avitum AG, Melsungen (DE)

(72) Inventor: Enrico Corazzari, Mirandola (IT)

(73) Assignee: B. Braun Avitum AG, Melsungen (DE)

(*) Notice: Subject to any disclaimer, the term of this patent is extended or adjusted under 35 U.S.C. 154(b) by 318 days.

(21) Appl. No.: 18/590,195

(22) Filed: Feb. 28, 2024

(65) Prior Publication Data

US 2024/0316252 A1 Sep. 26, 2024

(30) Foreign Application Priority Data

Mar. 3, 2023 (EP) .................................... 23159882

(51) Int. Cl.

*A61M 1/14* (2006.01)
*A61M 1/34* (2006.01)
*A61M 1/16* (2006.01)

(52) U.S. Cl.

CPC ............... *A61M 1/14* (2013.01); *A61M 1/156* (2022.05); *A61M 1/1652* (2014.02); *A61M 1/34* (2013.01); *A61M 2209/082* (2013.01)

(58) Field of Classification Search

CPC ...... A61M 1/14; A61M 1/1652; A61M 1/156; A61M 1/34; A61M 2209/082

See application file for complete search history.

(56) References Cited

U.S. PATENT DOCUMENTS

| | | | | |
|---|---|---|---|---|
| 3,603,550 A * | 9/1971 | Byrd | A62C 13/78 248/154 |
| 6,250,482 B1 * | 6/2001 | Want | A61M 1/61 5/503.1 |
| 8,182,440 B2 * | 5/2012 | Cruz | A61M 1/16 604/4.01 |
| 10,201,647 B2 * | 2/2019 | Norris | A61M 1/80 |
| 10,337,724 B2 * | 7/2019 | Schäfer | A61M 1/14 |
| 10,668,200 B2 * | 6/2020 | Krummenacher | A61B 50/20 |
| 11,752,248 B2 * | 9/2023 | Beavers | A61M 1/1522 604/6.11 |

(Continued)

FOREIGN PATENT DOCUMENTS

| | | |
|---|---|---|
| EP | 0611227 A1 | 8/1994 |
| EP | 2263714 A1 | 12/2010 |

(Continued)

OTHER PUBLICATIONS

Search Report received in European Application No. 23159882.2-1113 dated Jul. 6, 2023, 11 pages.

*Primary Examiner* — Guy K Townsend
(74) *Attorney, Agent, or Firm* — Christopher A. Rothe; CM Law

(57) ABSTRACT

A support member for an integrated blood treatment fluid module, comprising a base body configured to support a blood treatment device having a cylindrical casing, characterized by a handle permanently attached to the base body and configured to be manually gripped for handling the integrated blood treatment fluid module, wherein the handle comprises a concave seating surface configured to accommodate the cylindrical casing of the blood treatment device.

13 Claims, 5 Drawing Sheets

(56) References Cited

U.S. PATENT DOCUMENTS

Figure 1:
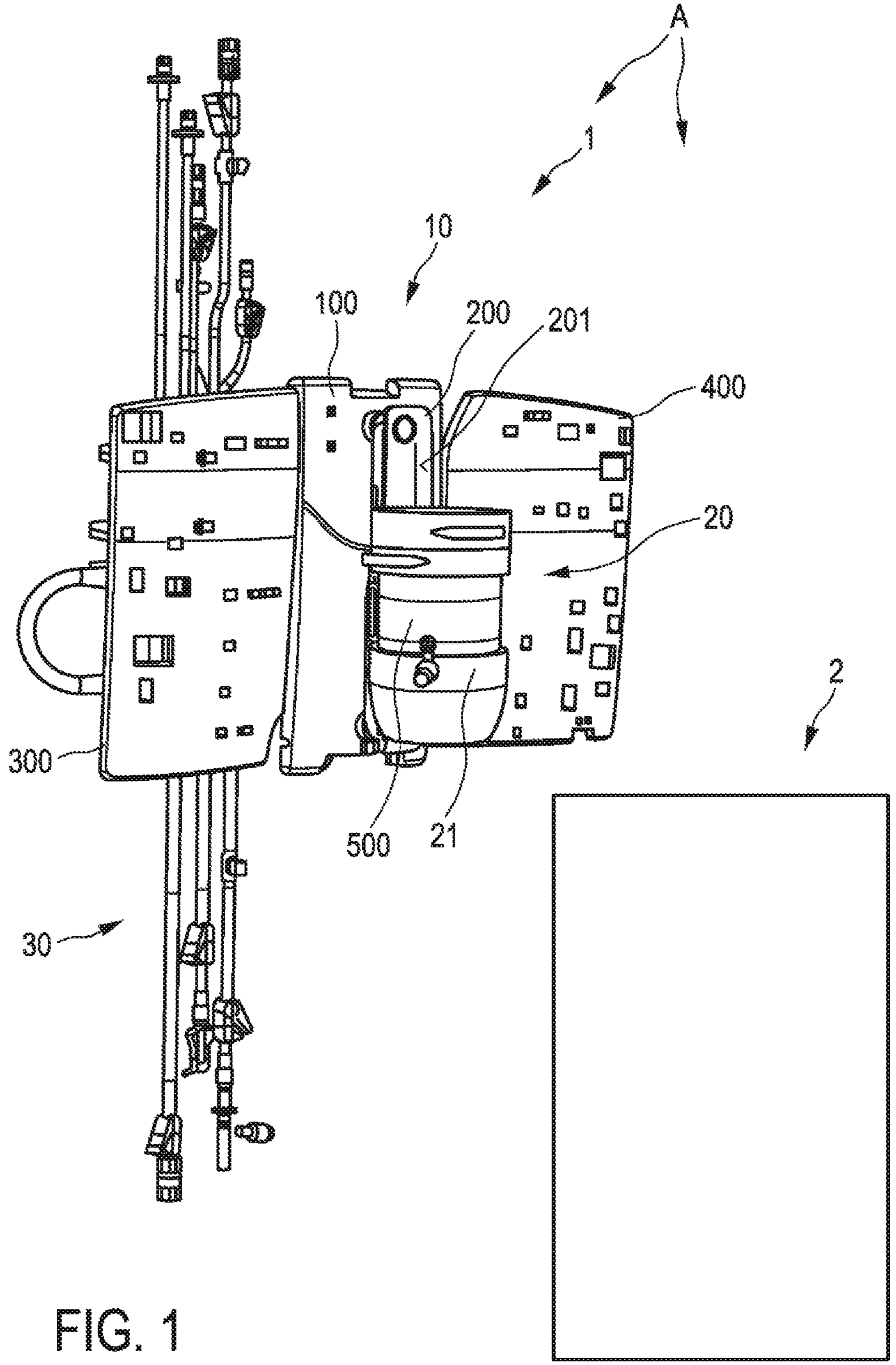

2004/0064080 A1* 4/2004 Cruz ....................... A61M 1/16
604/4.01
2010/0094192 A1* 4/2010 Peters ..................... A61M 1/34
604/6.09
2016/0101227 A1* 4/2016 Norris ................... A61M 1/155
604/29
2017/0246369 A1* 8/2017 Krummenacher ..... A61B 50/20
2024/0277928 A1* 8/2024 Epshteyn .............. A61M 1/154
2024/0316252 A1* 9/2024 Corazzari ............. A61M 1/156

FOREIGN PATENT DOCUMENTS

WO 0108722 A2 2/2001
WO WO-2016059589 A1 * 4/2016 .......... A61M 5/1415

* cited by examiner

Section A-A

SUPPORT MEMBER FOR AN INTEGRATED BLOOD TREATMENT FLUID MODULE

CROSS-REFERENCE TO RELATED APPLICATION

This application claims priority under 35 U.S.C. § 119 to European Application No. 23 159 882.2, filed on Mar. 3, 2023, the content of which is incorporated by reference herein in its entirety.

FIELD

The disclosure relates to a support member for an integrated blood treatment fluid module, comprising a base body configured to support a blood treatment device having a cylindrical casing.

Moreover, the disclosure relates to an integrated blood treatment fluid module comprising such a support member, to an apparatus for extracorporeal blood treatment comprising such an integrated blood treatment fluid module, and to a kit for setting up such an apparatus for extracorporeal blood treatment.

BACKGROUND

Extracorporeal blood treatment therapy typically involves drawing blood from a patient, extracorporeal treatment of the drawn blood by a blood treatment device and returning the treated blood to the patient.

Typical apparatuses for extracorporeal blood treatment comprise a main frame and an integrated blood treatment fluid module removably mounted on the main frame.

For example, EP 2 263 714 A1 discloses an integrated blood treatment fluid module comprising a blood treatment device with a cylindrical casing, namely a hemofilter or dialyzer, a fluid distribution circuitry in fluid communication with the blood treatment device, and a support member for supporting the blood treatment device and the fluid distribution circuitry. The support member of said prior art integrated module comprises a base body with connectors configured for receiving and permanently engaging with corresponding counter-connectors of the blood treatment device.

Further, EP 0 611 227 A1 discloses an integrated blood treatment fluid module comprising a support member and a blood treatment device with a cylindrical casing fixedly mounted on the support member to be movable between a retracted packaging position and an extended operating position.

Still further, WO 01/08722 A2 discloses an integrated blood treatment fluid module in the form of a filtration unit for a dialysis machine, comprising a hemofilter with a cylindrical casing provided with a number of first connecting elements, a support with a number of second connecting elements that can interact with the first connecting elements, and locking means for releasably locking the hemofilter on the support.

It is well-known that such integrated blood treatment fluid modules intend to facilitate the operation of blood treatment apparatuses, since both the setup before the start of treatment therapy and the necessary steps after the completion of the therapy can be performed quickly and reliably by an operator.

For mounting and dismounting from the main frame of the apparatus, the operator must safely handle the integrated blood treatment fluid module. Typically, the operator uses the casing of the blood treatment device for handling the entire module. To serve as a handling structure, the blood treatment device must be securely fastened to the support member and the casing must be sufficiently stable. Oftentimes, the blood treatment device is therefore permanently fastened to the support member factory-wise.

SUMMARY

It is an object of the disclosure to provide a support member of the type mentioned at the beginning, which allows for an improved handling, for a secure support of the blood treatment device and for reduced overall costs.

It is a further object of the disclosure to provide a kit that enables a facilitated setup of an apparatus for extracorporeal blood treatment.

It is a further object of the disclosure to provide an improved integrated blood treatment fluid module.

It is still a further object of the disclosure to provide an improved apparatus for extracorporeal blood treatment.

According to a first aspect, a support member for an integrated blood treatment fluid module is provided, the support member comprising a base body configured to support a blood treatment device having a cylindrical casing. The support member has a handle permanently attached to the base body and configured to be manually gripped for handling the integrated blood treatment fluid module, wherein the handle comprises a concave seating surface configured to accommodate the cylindrical casing of the blood treatment device.

The handle with its concave seating surface allows for a comfortable, ergonomic and safe handling and, at the same time, for a secure support of the blood treatment device on the base body. Consequently, the handle has two functions at the same time. On the one hand, the handle serves as a grip for the support member and thus for the entire integrated blood treatment fluid module. On the other hand, the handle simultaneously serves as a support structure for the blood treatment device. Due to the handle being permanently attached to the base body, there is no need to permanently attach the blood treatment device to the support member and/or its base body in order to serve as a handling structure. In contrast, the blood treatment device can be provided separately from the support member. The blood treatment device can be accommodated on the handle during a setup phase prior to starting the blood treatment therapy. In addition, it is possible to choose the blood treatment device from different blood treatment devices having different specifications. The specification of the blood treatment device can be chosen to fit the respective needs of the therapy or the patient. Hence, due to the disclosure, there is no need to provide different support members with permanently attached differently specified blood treatment devices. This allows for a simplified production process, reduced stock keeping at production facilities and medical facilities, and for an overall reduction of related costs.

The support member serves as a support structure for different components of the integrated blood treatment fluid module, for example the blood treatment device, a fluid distribution circuitry and/or possible other components. Together with said components, the support member forms the integrated blood treatment fluid module. The integrated blood treatment fluid module, in particular the support member, is configured to be mounted to a main frame of an apparatus for extracorporeal blood treatment. In one embodiment, the support member has a monolithic design, wherein the base body forms an integral portion of the support member. In one embodiment, the support member has a multi-part design, wherein the base body forms one part of the multi-part support member.

The blood treatment device can be, for example, a plasma filter, a hemodialysis filter, a hemofiltration filter, a hemodiafiltration filter or the like. The blood treatment device is not a component of the support element according to the disclosure. The blood treatment device comprises said, preferably circular, cylindrical casing. The cylindrical casing houses inner components of the blood treatment device, for example a filter component, a membrane component and/or possible other components. The cylindrical casing has a convex circumferential contour.

The handle is permanently attached to the base body, for example by bonding, welding or any other suitable joining technique. In one embodiment, the handle forms an integral portion of the base body. The concave seating surface is configured to accommodate the cylindrical casing. The seating surface is convex with respect to a transverse axis of the handle and with this also with respect to a transverse axis of the blood treatment device. The concave shape of the seating surface allows for a stable accommodation of the cylindrical casing. In particular, the interaction between the concave seating surface and the cylindrical casing counteracts relative movements along the transverse axis.

In one embodiment, the handle comprises at least one fastening portion configured to accommodate at least one fastening member to releasably fasten the cylindrical casing to the concave seating surface of the handle. This counteracts an unintentional loosening of the blood treatment device from the handle and allows for a yet improved safety. The fastening portion can, for example, be a slot, a hook, an eyelet or the like. The fastening member can, for example, be a strap, a latch, a hook-and-loop fastening strip or the like.

In one embodiment, the fastening portion is a slot extending continuously between lateral surfaces of the handle opposing each other along a transverse axis, wherein the slot is configured to accommodate a hook-and-loop fastening strip. This embodiment allows for a simple and at the same time reliable releasable fastening of the blood treatment device. In one embodiment, the hook-and-loop fastening strip is a component of the support member and/or the integrated blood treatment fluid module. For fastening the blood treatment device to the handle, the hook-and-loop fastening strip is put through the slot and around the cylindrical casing by forming a closed loop. The transverse axis is perpendicular to a longitudinal axis. The handle is elongated along the longitudinal axis. The same applies, mutatis mutandis, to the blood treatment device.

In one embodiment, the handle is elongated between a first end and a second end along a longitudinal axis, wherein the handle comprises at least one end stop portion arranged at the first end or at the second end, and wherein the end stop portion is configured to restrain a relative movability of the cylindrical casing along the longitudinal axis. The end stop portion prevents the cylindrical casing from moving along the longitudinal axis. In an operating state, the longitudinal axis is preferably parallel to a vertical spatial axis such that the end stop portion prevents the cylindrical casing from sliding downwards with gravity. The longitudinal axis is perpendicular to a transverse axis. The seating surface of the handle is concave with respect to the transverse axis. Preferably, the seating surface is planar with respect to the longitudinal axis. In one embodiment, the handle has a multi-part design, wherein the end stop portion forms one part of the multi-part handle. In one embodiment, the handle has a monolithic design, wherein the end stop portion is an integral portion of the handle. In an accommodated state of the cylindrical casing, the end stop portion is in contact with an end surface of the cylindrical casing. Preferably, the handle comprises a single end stop portion at only one of its ends. This facilitates the accommodation of differently sized blood treatment devices on the concave seating surface.

In one embodiment, the end stop portion is a rib protruding from the concave seating surface and configured to contact an end surface of the cylindrical casing. Preferably, the rib protrudes in a normal direction of the concave seating surface.

In one embodiment, the handle comprises a back surface opposing the concave seating surface, wherein the back surface of the handle is offset from a front surface of the base body to form a finger passage for the fingers of a hand of an operator while gripping the handle. The finger passage allows for a comfortable, ergonomic and secure gripping of the handle. The finger passage extends between the back surface of the handle and the front surface of the base body as well as between lateral surfaces of the handle opposing each other along the transverse axis. In order to handle the support member and/or the integrated blood treatment fluid module, the operator puts the fingers of one hand through the finger passage while his thumb presses onto the concave seating surface. If the blood treatment device is already mounted on the support member, the thumb may instead press onto the cylindrical casing covering the concave seating surface.

In one embodiment, the handle comprises at least one spacer and attachment portion protruding from the back surface, wherein the at least one spacer and attachment portion is permanently attached to the front surface of the base body by forming said finger passage. This is a simple and yet robust design. The spacer and adjustment portion can have any suitable form and size. In one embodiment, the spacer and attachment portion is one part of the handle, the handle having a multi-part design. In one embodiment, the spacer and attachment portion is an integral portion of the handle, the handle having a monolithic design. The at least one spacer and attachment portion is permanently attached to the front surface by a suitable joining technique, for example welding, bonding or the like. As an alternative or in addition, permanent attachment can be achieved by means of a permanent snap fit between the spacer and attachment portion and a complementary portion of the front surface.

In one embodiment, the handle comprises a first spacer and attachment portion and a second spacer and attachment portion, particularly each in the form of a cylindrical pin, being arranged at longitudinally opposing ends of the handle. Both spacer and attachment portions protrude into the direction of the front surface of the base body. Providing two spacer and attachment portions at longitudinally opposing ends of the handle results in a very robust design and allows for a particularly secure handling of the support member and secure accommodation of the blood treatment device.

According to a second aspect, a kit for setting up an apparatus for extracorporeal blood treatment is provided, the kit comprising: a support member according to the first aspect of the disclosure; and a set of different blood treatment devices having differently sized cylindrical casings with different diameters: wherein the concave seating surface of the handle of the support member has a curvature radius being large enough to accommodate the largest size cylindrical casing of the set of different blood treatment devices, such that each of the different blood treatment devices of the set can be selectively supported on the support member. The kit allows to choose one of the different blood treatment devices according to the needs of the particular extracorporeal blood treatment therapy or of the patient and to accommodate said blood treatment device on the concave seating surface of the handle. The curvature radius of the concave seating surface is large enough to accommodate any one of the differently sized cylindrical casings. The kit allows for a simplified setup, a simplified production process, reduced stockkeeping, and for a reduction of related costs.

According to a third aspect, an integrated blood treatment fluid module for an apparatus for extracorporeal blood treatment is provided, the integrated blood treatment fluid module comprising: a support member according to the first aspect of the disclosure: a blood treatment device with a cylindrical casing releasably accommodated on the concave seating surface of the handle of the support member; and a fluid distribution circuitry configured for fluid communication with the blood treatment device and supported on the support member.

According to a fourth aspect, an apparatus for extracorporeal blood treatment is provided, the apparatus having a main frame and an integrated blood treatment fluid module according to the third aspect of the disclosure, wherein the integrated blood treatment fluid module is releasably mounted to the main frame.

BRIEF DESCRIPTION OF THE DRAWING FIGURES

Figure 2:
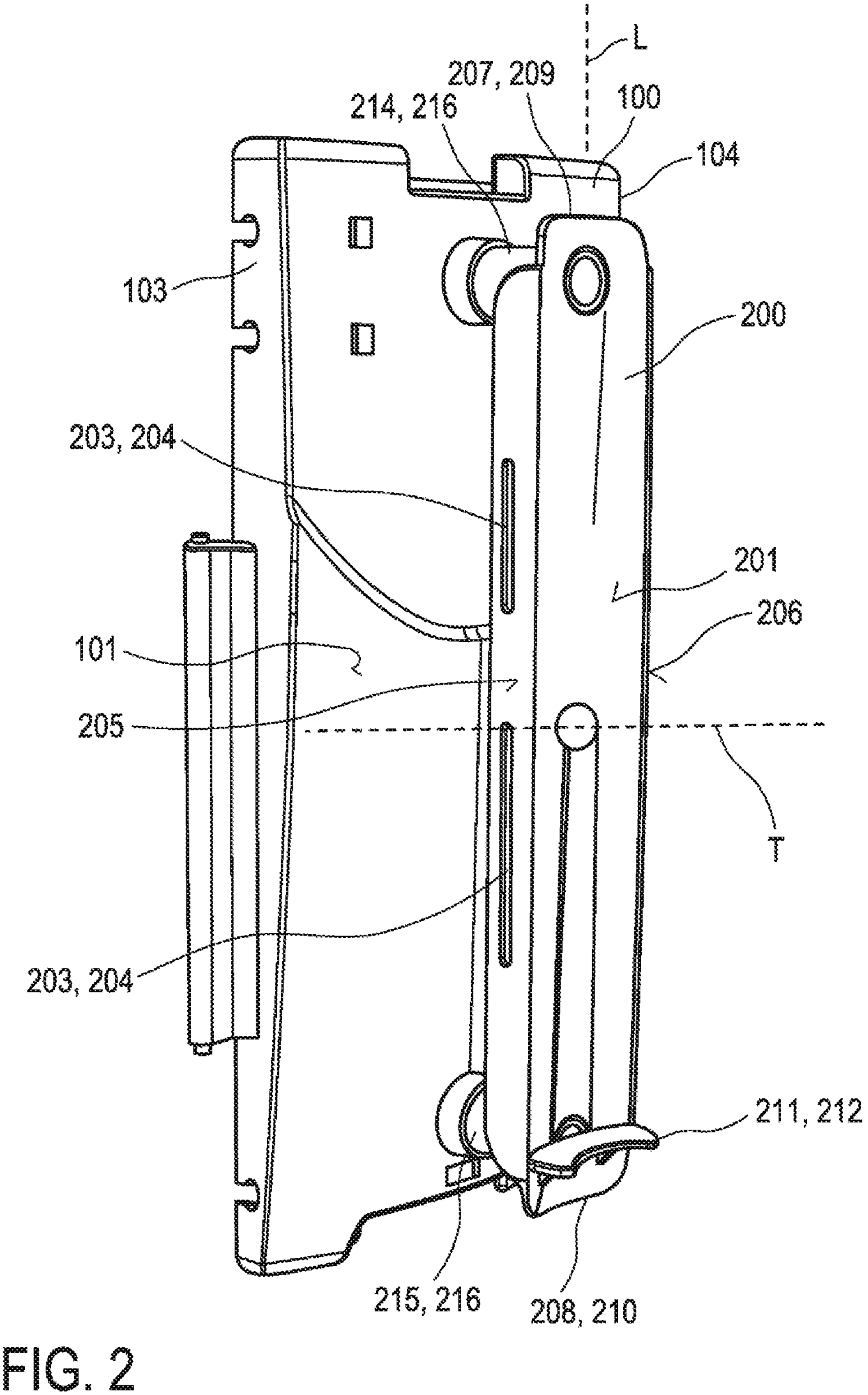
Figure 3:
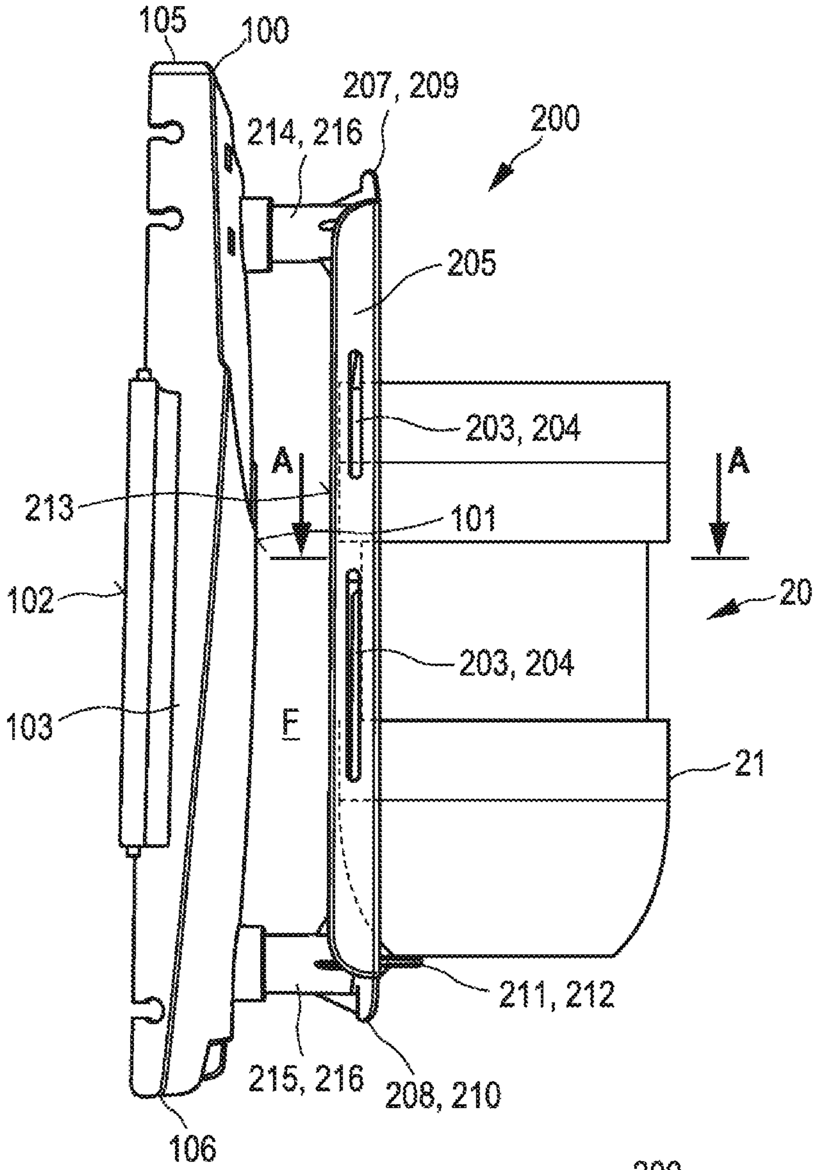
Figure 3A:
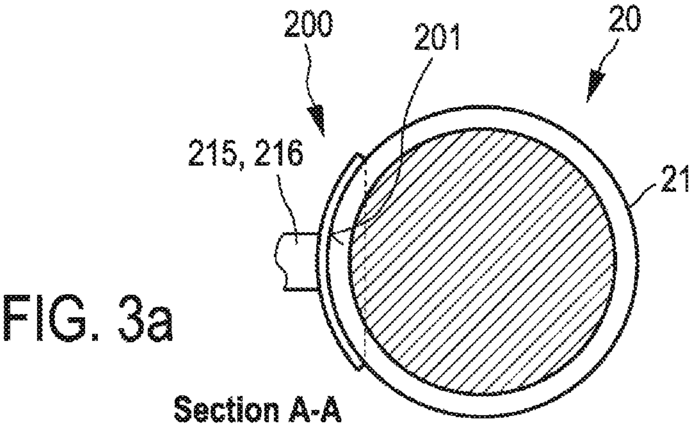
Figure 4:
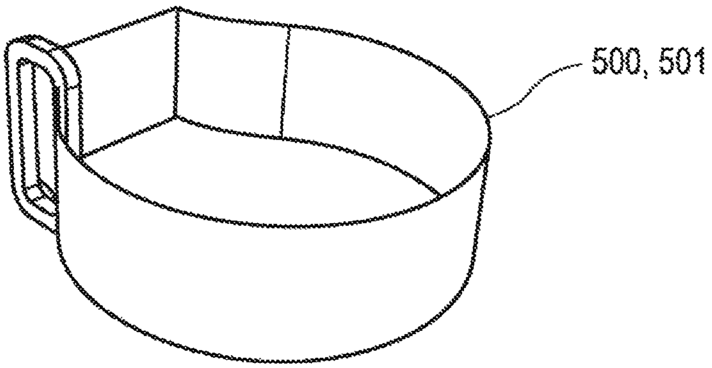

In the following, preferred exemplary embodiments of the disclosure will be described in detail with reference to the drawings. Throughout the drawings, the same elements will be denoted by the same reference numerals. The drawings schematically show:

FIG. 1 a perspective view of one embodiment of an apparatus for extracorporeal blood treatment having one embodiment of an integrated blood treatment fluid module which comprises one embodiment of a support member;

FIG. 2 a perspective view of a base body and a handle of the support member shown in FIG. 1:

FIG. 3 a side view of the base body and the handle shown in FIG. 2, together with a blood treatment device of the apparatus:

FIG. 3*a* a cross-sectional view along a section A-A according to FIG. 3:

FIG. 4 a detailed perspective view of a fastening member configured to releasably fasten the blood treatment device to the handle shown in FIGS. 2, 3, 3*a:*

Figure 5:
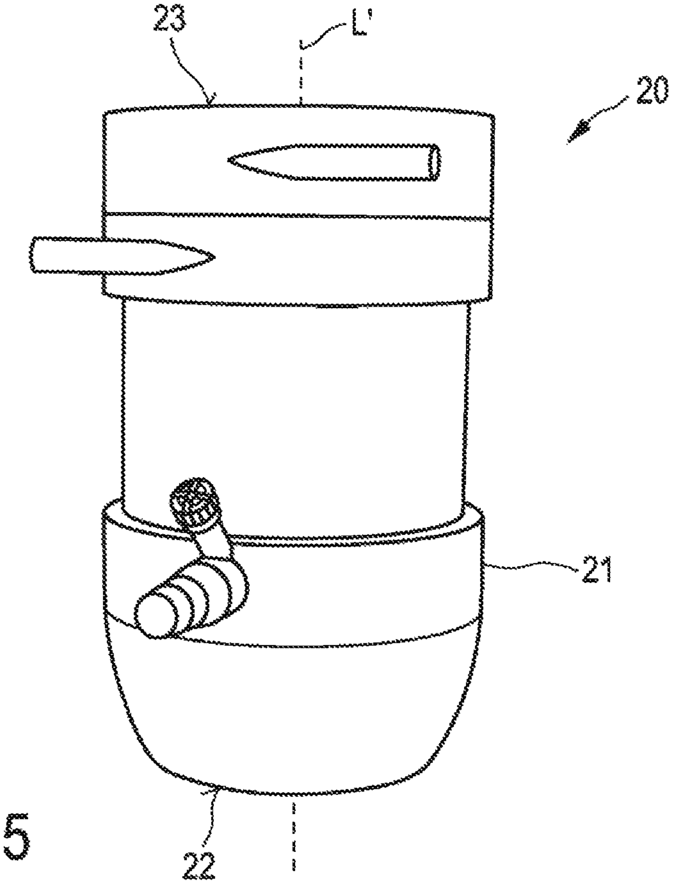

FIG. 5 a detailed perspective view of the blood treatment device of the integrated blood treatment fluid module shown in FIGS. 1, 3, 3*a*, and FIG. 6 a perspective simplified view of one embodiment of a kit for setting up the apparatus shown in FIG. 1.

DETAILED DESCRIPTION

According to FIG. 1, an apparatus A for extracorporeal blood treatment is provided to carry out a therapeutic treatment, for example a blood purification and water removal in the case of renal failure. The apparatus A comprises an integrated blood treatment fluid module 1 and a main frame 2. The main frame 2 is depicted in schematically simplified manner.

The integrated blood treatment fluid module 1 can be mounted on the main frame 2 in a way that reduces pre- and post-therapy handling and fluid interconnection requirements.

The integrated blood treatment fluid module 1 comprises a support member 10, a blood treatment device 20 and a fluid distribution circuitry 30.

The support member 10 comprises a base body 100 configured to support the blood treatment device 20. In the illustrated embodiment, the support member 10 further comprises a first side body 300 and a second side body 400, both side bodies 300, 400 being optional and hingedly connected to the base body 100.

The blood treatment device 20 comprises a cylindrical casing 21, the cylindrical casing 21 containing internal components, for example filter components, membrane components or the like. In the illustrated embodiment, the blood treatment device 20 is a dialyzer.

The fluid distribution circuitry 30 is supported on the support member 10 and comprises different fluid circuits (without reference signs), wherein at least one of the fluid circuits of the fluid distribution circuitry 30 can be fluidly connected to the blood treatment device 20.

The general function of the blood treatment device 20 and the fluid distribution circuitry 30 is well-known to a skilled person and not within the focus of the present disclosure. It is therefore not necessary to give further details on the structure and/or function of the blood treatment device 20 and the fluid distribution circuitry 30.

The support member 10 further comprises a handle 200 (see also FIG. 2, 3). The handle 200 is permanently attached to the base body 100. The handle 200 is configured to be manually gripped for handling the integrated blood treatment fluid module 1. Moreover, the handle 200 comprises a concave seating surface 201 configured to accommodate the blood treatment device 20 (see also FIG. 3*a*). In particular, the concave seating surface 201 is configured to accommodate the cylindrical casing 21 of the blood treatment device 20. The handle 200 therefore has two functions at the same time. On the one hand, the handle 200 serves as a support structure for the blood treatment device 20. On the other hand, the handle 200 serves as a grip and/or gripping structure for handling the support member 10 and thus the entire integrated blood treatment fluid module 1.

Since the handle 200 is permanently attached to the base body 100, there is—in contrast to some prior art solutions-no need to permanently attach the blood treatment device 20 to the support member 10 in order to serve as a gripping structure. The blood treatment device 20 can therefore be provided separately from the support member 10. In the illustrated embodiment, the blood treatment device 20 is accommodated on the handle 200 just prior to starting the therapy, i.e. during a setup phase of the apparatus A. It is therefore possible to choose the blood treatment device 20 according to the needs of the respective therapy or the patient to be treated.

In the illustrated embodiment, the support member 10 further comprises a fastening member 500 configured to releasably fasten the blood treatment device 20 to the handle. In particular, the fastening member 500 is configured to releasably fasten the cylindrical casing 21 to the concave seating surface 201. The fastening member 500 interacts with a fastening portion 203 of the handle 200. The fastening portion 203 is configured to accommodate the fastening member 500.

In the illustrated embodiment, the fastening portion 203 is a slot 204 and the fastening member 500 is a hook-and-loop fastening strip 501.

The slot 204 extends continuously between lateral surfaces 205, 206 of the handle. The lateral surfaces 205, 206 oppose each other along a transverse axis T of the handle

200. The lateral surfaces 205, 206 can also be referred to as left lateral surface 205 and right lateral surface 206. In order to releasably fasten the blood treatment device 20 to the handle 200, the hook-and-loop fastening strip 501 is put through the slot and around the cylindrical casing 21 in order to form a closed loop. Said closed loop and/or the hook-and-loop fastening strip 501 can be opened and closed in well-known manner.

The concave seating surface 201 prevents relative movements of the cylindrical casing 21 along the transverse axis T.

In the illustrated embodiment, the handle 200 comprises two fastening portions 203 and with this two slots 204. Referring to FIGS. 2, 3, said fastening portions 203 and/or slots 204 can be referred to as upper and lower fastening portion/slot. Depending on the form and size of the blood treatment device used, the upper, the lower or both of said fastening portions can be used to accommodate the fastening member 500. Of course, it is also possible to use two fastening members, one with each fastening portion.

In the illustrated embodiment, the handle 200 is elongated along a longitudinal axis L between a first end 207 and a second end 208. The longitudinal axis L is perpendicular to the transverse axis T.

The concave seating surface 201 is concave with respect to the transverse axis T. In the embodiment illustrated, the concave seating surface 201 is planar with respect to the longitudinal axis L. When accommodated on the concave seating surface 201, a longitudinal axis L' (see FIG. 5) of the cylindrical casing 21 is parallel to the longitudinal axis L of the handle.

The first end 207 can also be referred to as upper end 209. The second end 208 can also be referred to as lower end 210. When the support member 10 is mounted on the main frame 2 of the apparatus A, the longitudinal axis L is parallel to a vertical axis or height axis (without reference sign) of the main frame 2 and/or to a vector of gravity (without reference sign).

In order to prevent the blood treatment device 20 from sliding downwards the handle 200, an end stop portion 211 is provided and arranged at the second end 208. The end stop portion 211 is configured to restrain a relative movability of the cylindrical casing 21 along the longitudinal axis L in downward direction. The end stop portion 211 is configured to contact an end surface 22 of the cylindrical casing 21 (see FIG. 5). The cylindrical casing 21 extends along the longitudinal axis L' between the end surface 22, which is a lower end surface, and an opposing end surface 23. The opposing end surface 23 forms an upper end surface of the cylindrical casing 21.

In the illustrated embodiment, the end stop portion 211 is a rib 212 protruding from the concave seating surface 201. The rib 212 protrudes substantially perpendicular to the transverse axis T and substantially perpendicular to the longitudinal axis L. In the illustrated embodiment, the rib 212 protrudes substantially in normal direction of the concave seating surface 201.

It is worth mentioning that the handle 200 does not comprise a further end stop portion arranged at the upper end 209. This allows the use of large size blood treatment devices with cylindrical casings rising above the upper end 209.

The base body 100 comprises a front surface 101, an opposing back surface 202, lateral surfaces 103, 104 opposing each other along the transverse axis T and upper and lower surfaces 105, 106 opposing each other along the longitudinal axis L. In the illustrated embodiment, the base body 100 has a plate like structure and form extending mainly along the longitudinal axis L and the transverse axis T and being flat in a direction perpendicular to both of said axes L, T.

The handle 200 is arranged on the front surface 101. The back surface 102 is configured to engage a front surface (without reference sign) of the main frame 2. The opposing lateral surfaces 103, 104 each form a hinged connection to said side bodies 300, 400.

The handle 200 comprises a back surface 213 opposing the concave seating surface 201 and being offset to the front surface 101 of the base body 100. The offset between the back surface 213 and the front surface 101 forms a finger passage F between the handle 200 and the base body 100. The finger passage F is configured to accommodate the fingers of a hand of an operator while gripping the handle 200. The finger passage F extends between the opposing lateral sides 205, 206 of the handle 200, and between the first end 207 and the second end 208.

In the illustrated embodiment, the handle 200 comprises at least one spacer and attachment portion 214. The spacer and attachment portion 214 protrudes from the back surface 213 and is, in particular permanently, attached to the base body by forming said offset between the back surface 213 and the front surface 101. The spacer and attachment portion 214 serves as attachment means and—at the same time—as spacing means for attaching the handle 200 to and spacing the handle 200 from the base body 100.

In the illustrated embodiment, the handle 200 comprises a further spacer and attachment portion 215. The spacer and attachment portion 214, 215 can also be referred to as upper spacer and attachment portion 214 and lower spacer and attachment portion 215. The upper spacer and attachment portion 214 is arranged at the upper end 209. The lower spacer and attachment portion 215 is arranged at the lower end 210 of the handle 200. Both spacer and attachment portions 214, 215 are in the form of a cylindrical pin 216. Both pins 216 extend between the back surface 213 of the handle 200 and the front surface 101 of the base body 100.

As already mentioned, the handle 200 is permanently attached to the base body 100. In the illustrated embodiment, the support member 10 has a multi-part design, wherein the base body 100 and the handle 200 form different parts of said multi-part design. Both parts, i.e., the base body 100 and the handle 200, are permanently attached to each other by means of a suitable joining technique. For example, the handle 200 can be permanently bonded by welding or gluing. In addition or as an alternative, the handle 200 can be permanently attached to the base body by means of a permanent snap fit connection or the like. In the illustrated embodiment, said spacer and attachment portions 214, 215 are permanently bonded to complementary receptacles (without reference signs) formed on the front surface 101.

In an embodiment not illustrated in the drawings, the support member has a monolithic design, wherein the handle forms an integral portion of the monolithic support member.

Figure 6:
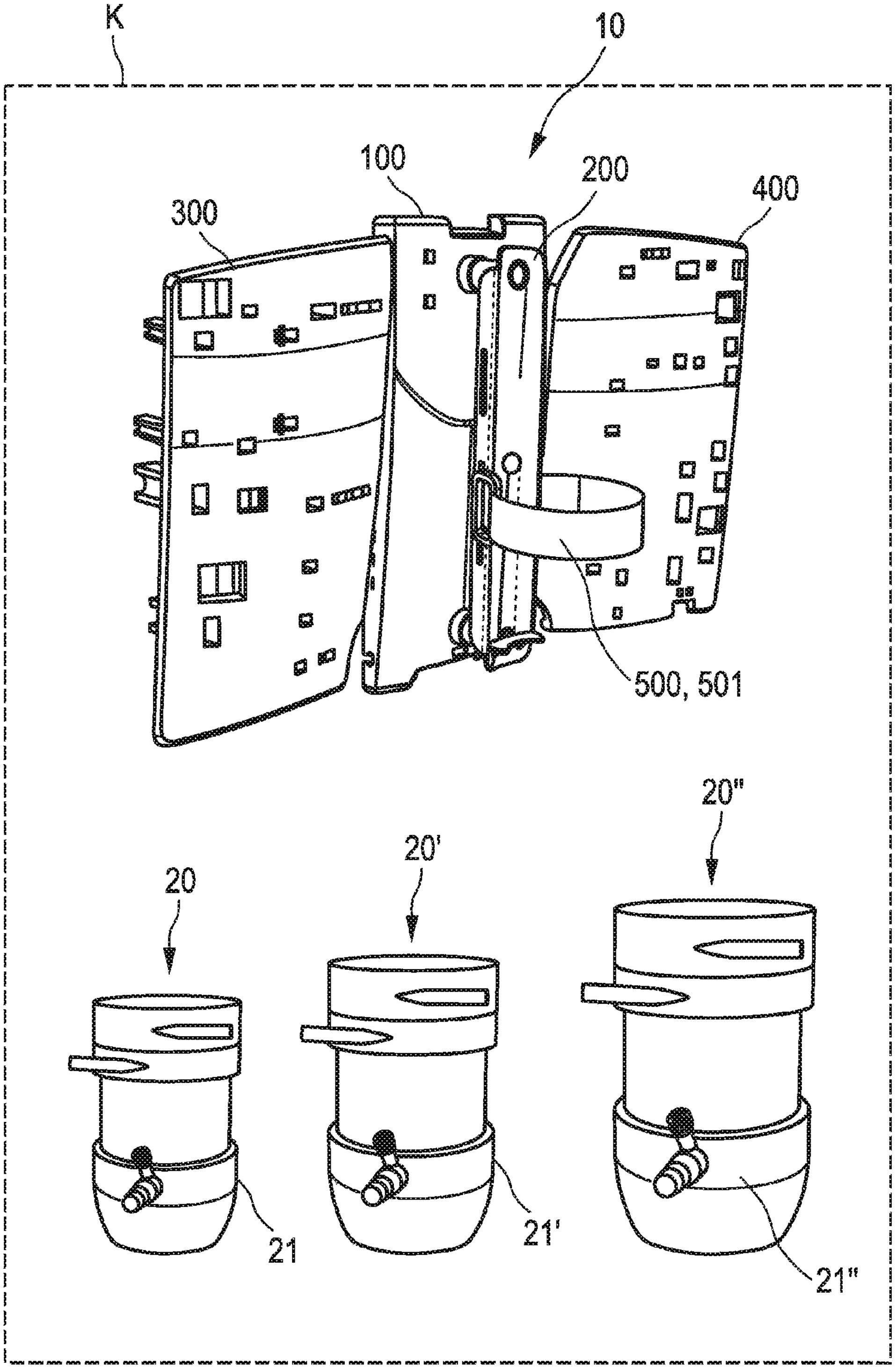

FIG. 6 shows a kit K comprising the support member 10 and a set of different blood treatment devices 20, 20', 20" having differently sized cylindrical casings 21, 21', 21".

The different blood treatment devices 20, 20', 20" can also be referred to as small size device 20, medium size device 20' and large size device 20". The same applies, mutatis mutandis, regarding the differently sized cylindrical casings 21, 21', 21".

The support member 10, as already mentioned, comprises the base body 100, the handle 200 and the optional side bodies 300, 400. The support member 10 further comprises the fastening member 500.

Depending on the needs of the specific blood treatment therapy carried out with the extracorporeal blood treatment apparatus A, the operator can choose one of the different blood treatment devices 20, 20', 20". The handle 200 is configured to selectively support each of the differently sized blood treatment devices 20, 20', 20". To this end, a curvature radius (without reference sign) of the concave seating surface 201 is large enough to accommodate the largest size cylindrical casing 21".

The invention claimed is:

1. A support member for an integrated blood treatment fluid module, the support member comprising:

a base body configured to support at least one blood treatment device having a cylindrical casing; and a handle permanently attached to the base body, the handle configured to be manually gripped for handling the integrated blood treatment fluid module, and the handle comprising a concave seating surface configured to accommodate the cylindrical casing of the at least one blood treatment device, wherein the handle is elongated between a first end and a second end along a longitudinal axis, wherein the handle comprises at least one end stop portion arranged at the first end or at the second end, and wherein the at least one end stop portion is configured to restrain a relative movability of the cylindrical casing along the longitudinal axis.

2. The support member according to claim 1, wherein the handle comprises at least one fastening portion configured to accommodate at least one fastening member to releasably fasten the cylindrical casing to the concave seating surface of the handle.

3. The support member according to claim 2, wherein the at least one fastening portion is a slot extending continuously between lateral surfaces of the handle opposing each other along a transverse axis, wherein the slot is configured to accommodate a hook-and-loop fastening strip.

4. The support member according to claim 1, wherein the at least one end stop portion is a rib protruding from the concave seating surface and configured to contact an end surface of the cylindrical casing.

5. The support member according to claim 1, wherein the handle comprises a back surface opposing the concave seating surface, wherein the back surface is offset from a front surface of the base body to form a finger passage for fingers of a hand of an operator while gripping the handle.

6. The support member according to claim 5, wherein the handle comprises at least one spacer and attachment portion protruding from the back surface, wherein the at least one spacer and attachment portion is permanently attached to the front surface by forming said finger passage.

7. The support member according to claim 6, wherein the handle comprises:

a first spacer and attachment portion at a first end of the handle; and a second spacer and attachment portion at a second end of the handle, the first end and the second end being longitudinally opposing ends of the handle.

8. A kit for setting up an apparatus for extracorporeal blood treatment, the kit comprising:

the support member according to claim 1; and wherein the at least one blood treatment device comprises a set of different blood treatment devices having differently sized cylindrical casings with different diameters;

wherein the concave seating surface of the handle of the support member has a curvature radius large enough to accommodate a largest cylindrical casing of the differently sized cylindrical casings such that each blood treatment device of the set of different blood treatment devices is selectively supportable on the support member.

9. An integrated blood treatment fluid module for an apparatus for extracorporeal blood treatment, the integrated blood treatment fluid module comprising:

the support member according to claim 1;

a first blood treatment device of the at least one blood treatment device with a first cylindrical casing releasably accommodated on the concave seating surface of the handle of the support member; and a fluid distribution circuitry configured for fluid communication with the first blood treatment device and supported on the support member.

10. An apparatus for extracorporeal blood treatment, the apparatus comprising:

the integrated blood treatment fluid module according to claim 9; and a main frame, the integrated blood treatment fluid module being releasably mounted to the main frame.

11. The support member according to claim 1, wherein the second end is located at vertical bottom of the handle when the handle is in a use position, and the at least one end stop portion is located between lateral surfaces of the handle opposing each other along a transverse axis, and extends away from the concave seating surface.

12. The support member according to claim 4, wherein the rib comprises a planar body extending perpendicular to a longitudinal axis of the concave seating surface.

13. The support member according to claim 1, wherein a distance between the first end of the handle and the second end of the handle is greater than a distance between a first end and a second end of a first blood treatment device of the at least one blood treatment device, to thereby accommodate the first blood treatment device along a first portion of the concave seating surface, with a second portion of the concave seating surface being exposed to be manually gripped for handling without gripping the first blood treatment device.

* * * * *